United States Patent [19]

Klein et al.

[11] 4,313,855

[45] Feb. 2, 1982

[54] FIXATIVE FOR PERFUME COMPOSITIONS

[75] Inventors: Erich Klein; Willi Rojahn, both of Holzminden, Fed. Rep. of Germany

[73] Assignee: Dragoco Gerberding & Co. GmbH, Holzminden, Fed. Rep. of Germany

[21] Appl. No.: 131,545

[22] Filed: Mar. 18, 1980

Related U.S. Application Data

[60] Division of Ser. No. 11,889, Feb. 13, 1979, Pat. No. 4,252,986, and a continuation-in-part of Ser. No. 11,889.

[30] Foreign Application Priority Data

Feb. 22, 1978 [DE] Fed. Rep. of Germany ....... 2807584

[51] Int. Cl.$^3$ .............................................. C11B 9/00
[52] U.S. Cl. .............................................. 252/522 R
[58] Field of Search ..................... 252/522 R; 568/822, 568/824

[56] References Cited

U.S. PATENT DOCUMENTS 3,996,296 12/1976 Mookherjee et al. .......... 252/522 R
4,072,719 2/1978 Naegeli .......................... 252/522 R
4,136,066 1/1979 DeHaan et al. ................. 252/522 R

FOREIGN PATENT DOCUMENTS 848690 9/1960 United Kingdom .

*Primary Examiner*—John F. Niebling
*Attorney, Agent, or Firm*—Browdy and Neimark

[57] ABSTRACT

A fixative for perfume compositions, 1-(2,6,6-trimethyl-cyclohexyl)-hexane-3-ol, itself odorless to many people, brings about a "rounding-off" of the perfume while increasing its intensity. The compound is made by condensation of citral with pentane-2-on, followed by cyclization and hydrogenation.

8 Claims, No Drawings

FIXATIVE FOR PERFUME COMPOSITIONS

CROSS-REFERENCE TO RELATED APPLICATION

The present application is a divisional-continuation-in-part of U.S. application Ser. No. 11,889, filed Feb. 13, 1979, now U.S. Pat. No. 4,252,986, the entire contents of which are hereby incorporated by reference.

FIELD OF THE INVENTION

The present invention relates to the new compound 1-(2,6,6-trimethyl-cyclohexyl)-hexane-3-ol having the structural formula I,

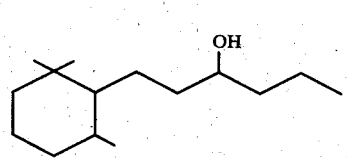

its manufacture, as well as its use as fixative for perfume compositions.

SUMMARY OF INVENTION

It has been found that an addition of 1-(2,6,6-trimethyl-cyclohexyl)-hexane-3-ol effectively brings about a "rounding-off" and fixation of perfume compositions while simultaneously increasing the intensity of the fragrance. The quantity used amounts usually to 1 to 25% by weight relative to the total composition, and a very distinct fixing effect can be ascertained particularly from approximately 3%. In principle, more than 25% may also be employed; this depends, however, upon the nature of the total composition and may be easily determined by routine experiments. The term "perfume composition" is meant to here define so-called perfume oil, in other words, the concentrate, which is then thinned to obtain a perfume, or which is used for scenting cosmetic products, for example, soaps, hair lotions or creams. Such a perfume oil contains, in addition to the fixative, odoriferous substances and volatile oils.

DETAILED DESCRIPTION OF EMBODIMENTS

The 1-(2,6,6-trimethylcyclohexyl)-hexane-3-ol itself is not to be considered as an odoriferous substance in the conventional sense as this saturated secondary alcohol has been found to be odorless, or only very slightly scented, by a significant number of the test persons who were asked to judge this substance, whereas other persons perceived an intensely radiating wood-like, slightly animalic-urinary odor.

Anosmia, i.e. the incapability to perceive smells, which numerous people have with respect to this new alcohol, may be compared with the effect of various very expensive animalic fixatives, such as musk and amber, whose scent can also be noticed only faintly by certain people, or not at all.

The occurrence of anosmia with respect to a specific substance, particularly in the area of perfumery, appears to always point out to particularly good fixative properties of a substance and holds true at least for all of the fixatives which have heretofore been employed in the manufacture of perfume compositions. These aforementioned advantageous properties of 1-(2,6,6-trimethylcyclohexyl)-hexane-3-ol distinguish this substance from the homologous products which have been known for a long time, such as iso-tetrahydromethylionol and n-tetrahydromethylionol, which do not develop any fixative effect and with regard to which also no cases of anosmia have been ascertained.

The product 1-(2,6,6-trimethylcyclohexyl)-hexane-3-ol may be obtained, analogous to the method disclosed in the Journal of the American Chemical Society 46, 119 (1924) and Helv. Chim. Acta 26, 2151 (1943), by condensation of citral with pentane-2-on in the presence of bases to 8,12-dimethyltrideca-5,7,11-tri-en-4-on, cyclization thereof with phosphoric acid, and subsequent total hydrogenation of the cyclization product. For example, the condensation may be carried out in the presence of alkali hydroxide, such as NaOH or KOH, e.g. in an alcoholic solution, at about room temperature, in an inert solvent. The cyclization may be carried out by a slow addition of phosphoric acid at slightly below room temperature, a subsequent slight heating to room temperature while stirring for several hours, and renewed slight heating to approximately 10° C. above room temperature again while stirring for several hours. The hydrogenation may suitably be carried out catalytically under pressure using, e.g. Raney nickel, and at a temperature rising to 150°–200° C.

The following examples show, on the one hand, the manufacture of the new compound 1-(2,6,6-trimethylcyclohexyl)-hexane-3-ol and, on the other hand, some formulations for the use of 1-(2,6,6-trimethylcyclohexyl)-hexane-3-ol as fixative in perfume oils.

EXAMPLE 1

Manufacture of 1(2,2,6-trimethylcyclohexyl)-hexane-3-ol

First Stage:

Dropped into 1,520 grams of citral and 1,720 grams of methyl-n-propyl ketone while stirring at a temperature of 20°–25° C., are 32 grams of sodium hydroxide dissolved in 200 ml methanol. The reaction medium is stirred at that temperature for 24 hours. Thereafter, neutralization is effected with 60 grams glacial acetic acid, the reaction water formed is separated, and the solvent as well as any excess of methyl-n-propyl ketone are distilled off. The reaction product is purified by distillation. The yield is 1.66 kilograms of 8,12-dimethyltrideca-5,7,12-tri-en-4-on.

Kp$_2$ (boiling point): 225° C., d$_4^{20}$=0.9134; n$_D^{20}$=1.5232.

Second Stage:

1.66 kilograms of 8,12-dimethyltrideca-5,7,12-tri-en-4-on dissolved in 3 kilograms benzene are dropped while stirring at 10°–15° C. into 1.66 kilograms phosphoric acid and the reaction mixture is stirred for 2 hours at 20° C. and thereafter for 3 hours at 30° C. Thereupon water is added, the aqueous phase is extracted twice with benzene, the benzene extract is neutrally washed with sodium carbonate solution, and the benzene is then removed by distillation. The reaction product is purified by distillation. The yield is 1.3 kilograms 1-(2′,6′,6′-trimethylcyclohex-2′-enyl)-hex-1-en-3-on.

Kp$_2$: 190° C., d$_4^{20}$=0.9389; n$_D^{20}$=1.4953.

Third Stage:

1.3 kilograms of 1-(2′,6′,6′-trimethylcyclohex-2′-enyl)-hex-1-en-3-on are hydrogenated in the presence of Raney nickel as catalyst at 100 atmospheres excess H$_2$ pressure, until 3 mol H$_2$ have been absorbed. In the course of the hydrogenation, the reaction temperature is increased to 180° C. The hydration product is purified by distillation. The yield is 1.1 kilogram 1-(2',6',6'-trimethylcyclohexyl)-hexane-3-ol.

Kp$_2$: 123° C., d$_4^{20}$: 0.9147; n$_D^{20}$=1.4720.

EXAMPLE 2

Rose Bouquet

| | |
|---|---|
| 300 grams | phenyl ethyl alcohol |
| 200 grams | citronellol |
| 100 grams | geraniol |
| 100 grams | phenyl ethyl acetate |
| 50 grams | aldehyde C 11 undecylene, 10% in DPG |
| 50 grams | geranium oil Bourbon |
| 50 grams | trichloro phenyl ethyl acetate |
| 40 grams | ionone beta |
| 30 grams | citronellyl acetate |
| 20 grams | aldehyde C 9, 10% in DPG |
| 20 grams | iron beta, 10% in DPG |
| 10 grams | 4-methyl-2-isobutenyl tetrahydro pyrane in a 10% DPG solution |
| 970 grams | |

When 30 grams 1-(2,6,6-trimethylcyclohexyl)-hexane-3-ol are added to the above mixture, it provides to the mixture a radiating fragrance which is noticeable for a considerably longer period of time than the fragrance or aroma of the above mixture without such addition.

EXAMPLE 3

Perfume Oil with an Exotic, Flowery Aroma

| | |
|---|---|
| 140 grams | phenyl ethyl alcohol |
| 100 grams | alpha-hexyl-cinnamic aldehyde |
| 100 grams | benzylacetate |
| 90 grams | hydroxy-citronellal |
| 85 grams | p-tert. butyl-α-methyl dihydrocinnamic aldehyde |
| 85 grams | French lavender oil 4 = /42% |
| 65 grams | nerol |
| 40 grams | cumarin |
| 40 grams | musk ketone |
| 40 grams | musk ambrette |
| 25 grams | linalool |
| 20 grams | amyl salicylate |
| 20 grams | eugenol |
| 20 grams | ylang-ylang oil extra |
| 15 grams | patchouli oil Singapore |
| 10 grams | vanillin |
| 5 grams | iron beta |
| 900 grams | |

An addition of 100 grams 1-(2,6,6-trimethylcyclohexyl)-hexane-3-ol intensifies the flowery aroma and imparts to the perfume a considerably longer adherence.

EXAMPLE 4

Perfume Oil with a Wood-like Powdery Aroma for Soaps

| | |
|---|---|
| 150 grams | benzyl benzoate |
| 100 grams | cumarin |
| 100 grams | geraniol |
| 100 grams | lavandin abrialis |
| 100 grams | linalyl acetate |
| 75 grams | phenyl ethyl alcohol |
| 65 grams | patchouli oil Sing. rect. |
| 50 grams | amyl salicylate |
| 50 grams | linalool |
| 35 grams | geranium oil Bourbon |
| 20 grams | alpha-hexyl-cinnamic aldehyde |
| 20 grams | East Indian sandalwood oil |
| 5 grams | anisealdehyde |
| 2 grams | aldehyde C 12 laurin |
| 872 grams | |

An addition of 228 grams 1-(2,6,6-trimethylcyclohexyl)-hexane-3-ol imparts to the previously somewhat dull and flat-smelling perfume composition a long-lasting, radiant and natural fragrance.

It will be obvious to those skilled in the art that various changes may be made without departing from the scope of the invention and the invention is not to be considered limited to what is described in the specification.

What is claimed is:

1. The method of use of the compound 1-(2,6,6-trimethylcyclohexyl)-hexane-3-ol comprising adding said compound to a composition as a fixative.

2. The method according to claim 1 wherein said compound is added in an amount of from 1 to 25% by weight relative to the total perfume composition.

3. A method according to claim 1, wherein said compound is used in an amount of from 3 to 10% by weight relative to the perfume composition.

4. The method according to claim 1 or 2 wherein said perfume composition is added to a cosmetic product for scenting.

5. A method according to claim 1 or 2, wherein said perfume composition is mixed or thinned with a conventional perfume carrier and is used as perfume or toilet water.

6. In a perfume composition comprising perfume components and a fixative, the improvement wherein the fixative is 1-(2,6,6-trimethylcyclohexyl)-hexane-3-ol.

7. In a cosmetic having a scenting agent therein, the improvement wherein said scenting agent is the perfume composition in accordance with claim 6.

8. In a perfume or toilet water comprising a perfume composition and a conventional perfume carrier, the improvement wherein said perfume composition is the perfume composition in accordance with claim 6.

* * * * *